United States Patent [19]

Lillig et al.

[11] 4,298,570
[45] Nov. 3, 1981

[54] TRAY SECTION FOR AUTOMATED SAMPLE HANDLING APPARATUS

[75] Inventors: John E. Lillig, Diamond Bar; Richard C. Meyer, La Habra, both of Calif.

[73] Assignee: Beckman Instruments, Inc., Fullerton, Calif.

[21] Appl. No.: 141,455

[22] Filed: Apr. 18, 1980

[51] Int. Cl.³ .......................... G01N 1/14; G01N 1/18
[52] U.S. Cl. .............................. 422/64; 422/65; 422/100; 422/104
[58] Field of Search ................. 23/230 R; 422/63, 64, 422/65, 100, 104; 141/130

[56] References Cited

U.S. PATENT DOCUMENTS

| | | | |
|---|---|---|---|
| 3,615,236 | 10/1971 | Tamm | 141/130 X |
| 3,617,222 | 11/1971 | Matte | 23/230 R |
| 3,687,632 | 8/1972 | Natelson | |
| 3,799,744 | 3/1974 | Jones | |
| 3,814,582 | 6/1974 | Rohrbaugh et al. | 23/230 R |
| 3,832,135 | 8/1974 | Drozdowski et al. | 23/230 R |
| 3,883,308 | 5/1975 | Matte | 23/230 B |
| 3,963,349 | 6/1976 | Albright et al. | 73/64.1 |
| 3,969,079 | 7/1976 | Catarious | 23/230 B |
| 4,011,048 | 3/1977 | Johnson et al. | |
| 4,058,367 | 11/1977 | Gilford | 422/67 |
| 4,111,304 | 9/1978 | Lucas | 222/541 |
| 4,123,173 | 10/1978 | Bullock et al. | 356/246 |
| 4,170,625 | 10/1979 | Welch | 422/64 |

*Primary Examiner*—Ronald Serwin
*Attorney, Agent, or Firm*—R. J. Steinmeyer; J. E. Vanderburgh; Timothy R. Schulte

[57] ABSTRACT

A containment apparatus for liquids. The device may be used with nephelometric instruments to contain sample liquids for serial dilution. The containment apparatus includes a tray section having a plurality of wells formed as an integral part of the tray section. The wells include well portions extending from the tray section such that the well portions are insertible into holes in the turntable rim to secure the tray section to the rim.

1 Claim, 6 Drawing Figures

TRAY SECTION FOR AUTOMATED SAMPLE HANDLING APPARATUS

BACKGROUND OF THE INVENTION

1. Field of the Invention

The invention relates to the field of automated conveyance and containment of a liquid. More particularly the invention relates to a special receptacle and conveyance apparatus. In still greater particularity, the invention relates to a tray type receptacle with means to draw out the contents thereof and convey those contents to specific locations. By way of further characterization but not by way of limitation thereto, the invention is an automated sample handling apparatus for use with a nephelometric analyzer.

2. Description of the Related Art

Many measuring and testing instruments, as for example, immunonephelometric instruments, such as that described in U.S. Pat. No. 4,157,871 issued on June 12, 1979, and incorporated herein by reference, require successive manipulations of a sample substance to be tested. These manipulations consume a great deal of operator time when a number of assays on many samples are performed. To obtain good results, an operator must repeat a number of steps in the proper sequence for each sample. Manual pipetting steps include the identification of a number of samples as well as numerous sample dilutions. Because the sample manipulations are usually done manually, operator fatique and boredom often result in erroneous results. Additionally, reduced operator morale due to fatigue and boredom generally contributes to a decrease in job performance resulting in increased operating costs for the laboratory. Also, manual manipulations consume a great deal of time often resulting in long delays to obtain results.

In an automated sample handling system the requirement of successive serial dilutions may present an access problem in that all diluted and original undiluted sample must be available to introduce into the reaction cell. The samples must thus be readily accessible to an automated pipette having well-defined mobility, and yet, because of space limitations, the sample tray must occupy a minimal space. Design of an automated system must thus allow access to sample, reagent, etc., and yet not be so large or cumbersome so as to hinder efficient operation or cause long delay times in sample dilution and its transfer to a reaction cell.

SUMMARY OF THE INVENTION

The invention is an automated sample handling apparatus to be used with a testing instrument. The device includes a sample containment apparatus which cooperates with an automated pipetting system to provide easy and quick access to the sample substance and other substances as necessary. The automated apparatus transports the sample substance and reagents to and from the reaction cell in the testing instrument.

Transporting apparatus is provided in the automated sample handling system for conveying the substances to and from the diluting and reaction areas. The transporting apparatus includes a track and at least one robot or car mounted on the track. Preferably, three cars are used: one to transfer the sample to the diluting well; one to transfer the diluted sample to the reaction cell; and one to transfer the reagent to the reaction cell. Because precise positioning of the cars on the track is important, a positioning apparatus includes optical sensors mounted on the cars. These sensors detect reflected light from the track and identify apertures which are located at predetermined points on the track. Each car is modular, self-contained, and easily detached from the rail for service or replacement. The automated pipette assembly or each car may be slightly different but all are mounted on the car assembly in an identical manner.

A means for containing sample substance and diluent includes a plurality of wells adapted for movement into vertical alignment with the automated pipettes. The wells are arranged in rows in removable tray sections which are disposable and fit into a movable turntable. The last row of wells fits into apertures in the turntable to allow for easy insertion and removal of each tray section. The apertures in the turntable are arranged in two concentric rows with the tray sections fitting into the interior concentric row and individual sample containers fitting into the outer concentric row of apertures. The movable turntable allows movement of the wells with respect to the automated pipettes so as to allow pipette access to the well contents.

DESCRIPTION OF THE PREFERRED EMBODIMENT

Figure 1:
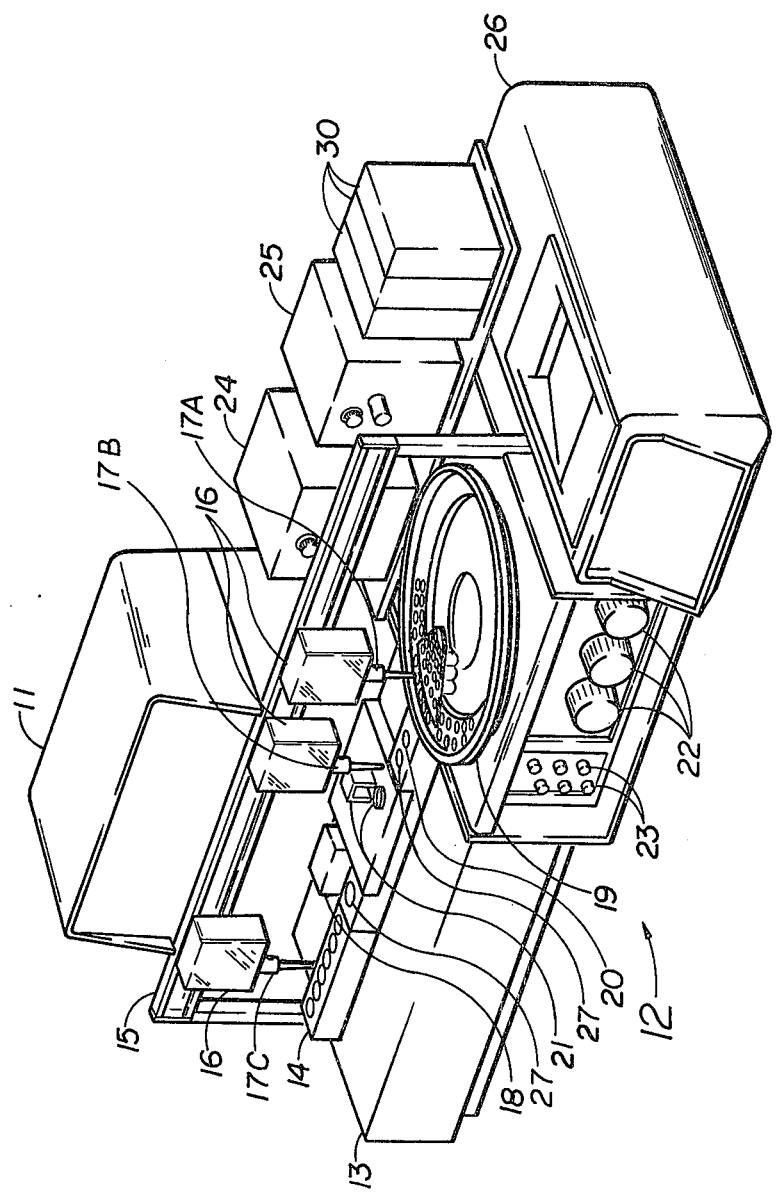
FIG. 1 is an overall perspective view of the automated sample handling apparatus in accordance with the present invention.

A better understanding of the invention may be had by referring to the drawing wherein like reference numerals denote like structure throughout each of the various figures. Referring to FIG. 1, a testing instrument 11 which may include a nephelometer is positioned adjacent an automated sample handling apparatus generally designated 12. Automated sample handling apparatus 12 includes a base 13 and a reagent bottle holder 14. A remotely controlled transporting means includes a movable car or cars 16 mounted on a track 15 which defines a traveling path therefor. Track 15 is mounted on base 13. An automated pipette 17A, B or C is mounted on each of cars 16.

A containing means which includes a turntable 19, is rotatably mounted on base 13 to allow automated pipette 17A or B access thereto. A card reader 18 and reaction cell 21 are mounted on base 13. Reaction cell 21 includes a flip-up cover. Antigen excess dilution wells 20 are mounted adjacent turntable 19. Peristaltic pumps 22 and fluid control valves 23 are also mounted on base 13. A source of diluent which may include a fixed ratio diluter 24 is mounted on base 13 adjacent turntable 19. A buffer dispenser 25 is mounted adjacent fixed ratio diluter 24. A data processor 26 is positioned adjacent the automated sample handling apparatus 12. Pipette wash stations 27 are mounted on base 13. A plurality of containers 30 containing diluent or other liquids are positioned adjacent diluter 24 and dispenser 25 and may be plumbed thereto.

Figure 2:
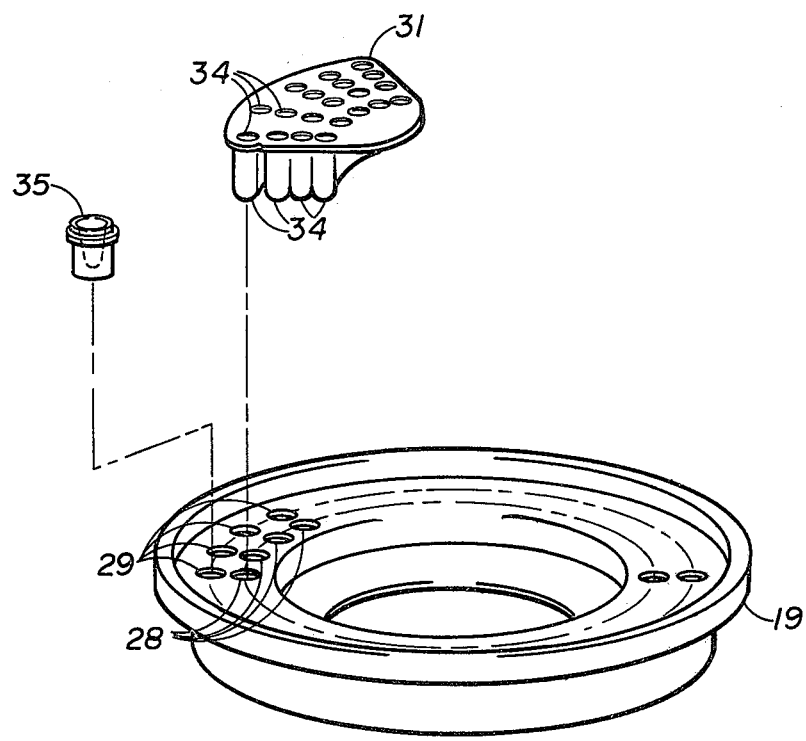
FIG. 2 is a perspective view of the turntable and removable tray.

Referring to FIG. 2, a containing means includes turntable 19 having an inner and outer concentric row of holes 28 and 29, respectively. A removable tray section 31 includes a plurality of wells 34. Wells 34 are open at the top of tray 31 to allow automated pipette access thereto. Wells 34 extend downwardly and are spaced apart to define a series of rows with a first row at the narrow innermost width portion of tray section 31 and a last row configured in a wider arc at a wide outermost width portion of removable tray section 31. The portions of wells 34 in the last row which extends downwardly from tray section 31 are spaced from the next to last row and from each other to allow each of these portions to be inserted into a hole in inner row of holes 28 as illustrated by the broken line in FIG. 2. A sample container 35 is insertible into outer row 29.

Figure 3:
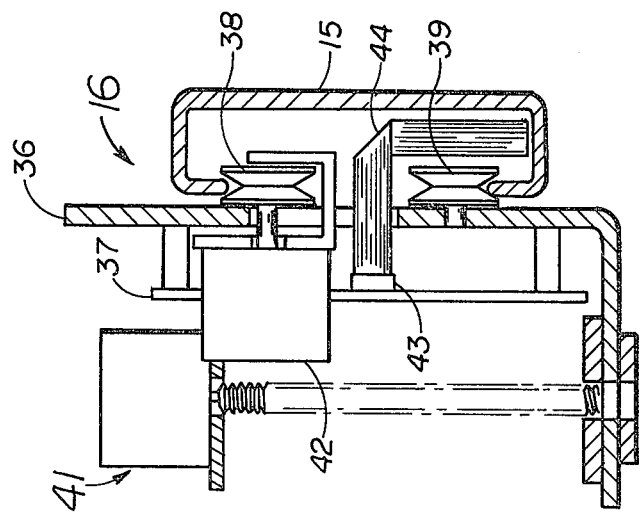
FIG. 3 is a partially sectioned side view of the track and car apparatus.

Referring to FIG. 3, a partially sectioned side view of the remotely controlled transporting apparatus is shown. Car 16 is mounted on track 15 and includes an L-shaped bracket 36 to support the component parts. Mounted on the vertical leg of L-shaped bracket 36 is a control board 37 containing all the necessary electronic circuitry to drive the associated apparatus. An upper wheel 38 and a pair of lower wheels 39 (only one shown) are mounted on the rear face of the vertical leg of L-shaped bracket 36. Upper wheel 38 and lower wheels 39 engage track 15. Lower wheels 39 are rotatably mounted on L-shaped bracket 36 while upper wheel 38 is part of a spring loaded assembly for horizontal drive. An elevator assembly 41 for vertical drive is mounted on a lower leg of L-shaped bracket 36. An automated pipette (not shown) attaches to elevator assembly 41. A stepper motor 42 drives upper wheel 38. Electrical power and control signals are supplied to control board 37 through a connector 43 and ribbon cable 44.

Figure 4:
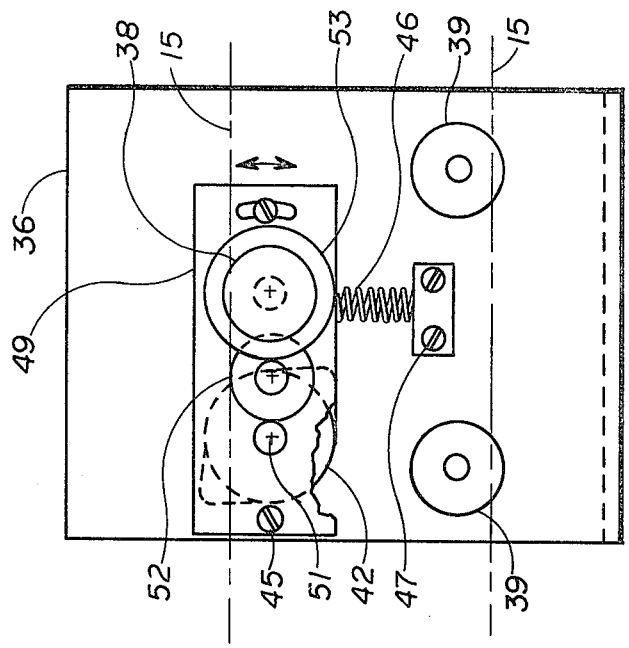
FIG. 4 shows a rear view of the horizontal car drive assembly.

Referring to FIG. 4, the horizontal drive assembly is shown as viewed from the rear. The assembly is mounted to L-shaped bracket 36 by a pivot 45 and is free to rotate in the direction indicated by the arrows. A spring 46 and a spring block 47 apply an upward force to the assembly. When lower wheels 39 are engaged with the lower lip of track 15, upper wheel 38 is wedged onto an upper lip of track 15. As upper wheel 38 is driven, the car travels along track 15. The drive is assembled to a drive bracket 49. The drive includes a stepper motor 42 and a pinion 51. An intermediate cluster gear 52 communicates between motor pinion 51 and a wheel gear 53 on wheel 38. The gear ratio from pinion 51 to the wheel is preferably 25:1. This gear ratio gives a fine motion resolution and amplifies the driving torque supplied by motor 42.

Figure 5:
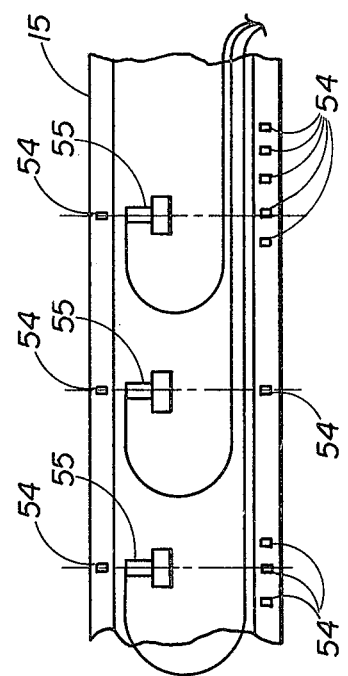
FIG. 5 shows the car positioning apparatus.

Referring to FIG. 5, a car positioning means includes a plurality of apertures 54 in track 15. A plurality of optical sensors 55 are mounted on control board 37 (shown in FIG. 3).

Figure 6:
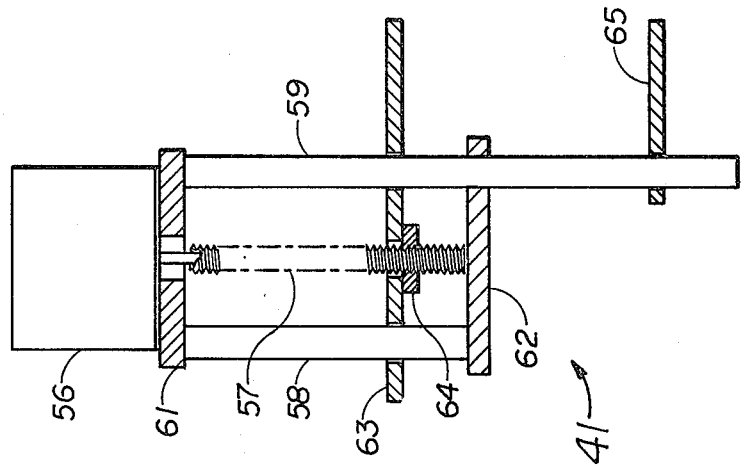
FIG. 6 shows the elevator mechanism for the automated pipette.

Referring to FIG. 6, elevator mechanism 41 is shown in detail. A stepper motor 56 has a lead screw 57 welded to its shaft. A support rod 58 and guide rod 59 separate a motor mount plate 61 from an assembly mount plate 62. A pipette mount plate 63 is journaled to slide freely up and down guide rod 59. A slot (not shown) engages support rod 58 preventing rotational freedom of plate 63. Mounted on plate 63 is a floating nut 64 which engages lead screw 57. Although not essential floating nut 64 is utilized to avoid high torque load due to binding, as small eccentricities exist with reasonable manufacturing tolerances. A lower pipette guide plate 65 establishes the position of the automated pipette.

MODE OF OPERATION

Referring to FIG. 1, base 13 is positioned adjacent nephelometer 11. Reaction cell 21 is the measuring site for nephelometer 11. Reaction cell 21, turntable 19, wash stations 27 and reagent bottle holder 14 are positioned along a path allowing automated pipettes 17 to access each location while traveling along track 15. While track 15 is shown as a straight line in the preferred embodiment, it should be understood that track 15 may be curved or angled or otherwise nonlinear.

The distance between reaction cell 21 and turntable 19 is known. Similarly, the distance between turntable 19 and other locations in the automated system are known. The vertical height of these locations is fixed such that they are all at approximately the same level. Thus, track 15 is suspended above base 13 a fixed distance therefrom to allow automated pipettes 17 on cars 16 to accurately travel the distance necessary to access the substances in locations such as reagent bottle holder 14, wash stations 27, reaction cell 21 and turntable 19.

Peristaltic pumps 22 provide rinse solutions to reaction cell 21 or automated pipettes 17 depending upon the state of fluid control valves 23. Fluid control valves 23 direct fluid flow by "pinching" off all the fluid lines except the one where fluid is required. Fluid is pushed through this line by a peristaltic pump 22 or buffer dispenser 25.

Automated sample handling system 12 is controlled by data processor 26. Data processor 26 contains a 24 digit alphanumeric display, printer, keyboard, and cassette program loader. The system program can be easily changed, by reading a new cassette, to several modes of operation. The operator interfaces with the system via the keyboard by responding to program questions. The operator sets up the assay, presses start and the instrument will perform the required motions to obtain and print out results. Because the system is automated, human error, which resulted from manual manipulation, is eliminated thus allowing for more accurate results. The automated system also allows the results to be obtained more quickly than with manual systems. All that is required of the operator is that he load the proper cassette into data processor 26. The data processor 26 prompts the operator to read from one to six antibody cards using card reader 18 and position antibody bottles in reagent rack 14. Following the last antibody card entry, data processor 26 prompts the reading of the calibrators until a calibrator is available for each assay being run. The operator then enters the turntable positions where the samples to be assayed are located along with the antibody bottle locations to identify which assays are to be run. The printer then prints a summary of the inputs and directs placement of any reagents needed. If no operator programming changes are required, the operator presses start and leaves the instrument.

Card reader 18 receives data from a card attached to each bottle of antibody or reagent in holder 14. Each card contains approximately forty unique parameters which automatically program the instrument with information such as: calibration constants; linearizing coefficients; signal conditioning constants; antigen excess criterion; units; noise discrimination; out of range limits; injection sequences; dilution requirements; etc.

The operation of the automated sample handling system results first in a cleaning of reaction cell 21 and priming of all input fluid lines and pipettes 17 with liquid. Dilutions of samples may be made using automated pipette 17A. Turntable 19 rotates such that pipette 17A can access the sample substance in one of the appropriate sample cups 35 (FIG. 2) located in one of the apertures in the outside ring 29 on turntable 19. Pipette 17A moves into position and lowers the pipette tip into the sample substance. The required amount of sample is drawn up into the pipette tip. Diluter pipette 17A is pulled up out of sample cup 35 (FIG. 2) and car 16 moves it over a dilution well 34 in removable tray section 31. This dilution well 34 is preferably in the outermost row of wells 34. Diluter pipette 17A is lowered into well 34 and the sample is delivered. Diluent is supplied to well 34 either from diluter 24 plumbed into pipette 17A or by other conventional means. Mixing of the sample and diluent is then accomplished by conventional apparatus such as by magnetic stir bars.

Following the last dilution of a particular sample, automated pipette 17B moves to a position over one of the wells 34 in the narrow row portion of removable tray section 31. Once in position automated pipette 17B lowers into well 34 and draws up the finally diluted sample. Automated pipette 17B then moves on track 15 to a position over reaction cell 21. Automated pipette 17B lowers and delivers the required amount of diluted sample into reaction cell 21 and moves to one of wash stations 27. A similar procedure is followed by automated pipette 17C which delivers the required amount of reagent from reagent bottle holder 14 to reaction cell 21. The timing is such that the antibody or reagent is delivered within seconds of the sample delivery.

When the correct amount of sample, diluent, and reagent have been delivered to reaction cell 21, the measurement is made. If antigen excess checking is required, automated pipette 17C will inject the appropriate check solution following the completion of the reaction. Reaction cell 21 is then drained, rinsed, and refilled with buffer for the next reaction.

Buffer substance can be dispensed into reaction cell 21 or directed to an automated pipette 17 if necessary, by the action of the fluid control valves 23. This allows buffer to be used as the diluent by dispensing the buffer into a dilution well on turntable 19, and then delivering a sample substance into that well. This becomes important when low dilutions of samples are required by an assay as is the case with drug assays. A great deal of nonspecific precipitation occurs once a diluted sample substance is injected into the buffer in reaction cell 21. This may affect the peak rate of the reaction causing errors in the result. Diluting the sample on turntable 19 with buffer allows this precipitation to occur before the sample is delivered to reaction cell 21, thus reducing the nonspecific precipitation to the point where it does not affect the peak rate. To this end fixed ratio diluter 24 is plumbed into a diluent source such as container 30 in order that a fixed dilution of any sample can be performed. A diluent delivery line from diluter 24 may be connected with automated pipette 17A to supply diluent to wells 34.

Referring to FIG. 3, cars 16 ride on track 15. The power to drive cars 16 is supplied through ribbon cables 44. Attached to each of ribbon cables 44 is a fluid line which connects with the automated pipette 17 mounted on each car 16. Ribbon cables 44 roll and unroll as cars 16 traverse track 15 horizontally. Ribbon cables 44 nest and pass by each other allowing nearly full travel for each car 16 from end to end of track 15.

In order to allow cars 16 to move on the same track 15, a positioning means is provided whereby each car can recognize designated positions on track 15 including a "home" position. The positioning means includes apertures 54 and optical sensors 55. Apertures 54 are spaced along the lips of track 15. Reflective optical sensors 55 mounted on control board 37 sense reflected light from these track lips. While only one optical sensor is shown for each car, two or more may be employed depending upon aperture placement. In the preferred embodiment, two optical sensors are used on each car 16, one to sense the upper lip of track 15 and one to sense the lower lip of track 15. When sensors 55 detect the metal of track 15, the signal is high. When apertures 54 are encountered, the signal is low because the light is no longer reflected from track 15.

The "home" position is important because, upon initiation of the apparatus, or if the cars should get lost these home positions provide a convenient way for the system to begin again. Lost cars could occur if the operator mispositions a car on the track. For each subsequent measurement each car will pass through its home position and all aperture counts per sequence must match a pre-defined number to ensure proper car travel. To find its respective home position each car is set in motion and compares incoming aperture information to a map in the system memory until it recognizes its position on track 15. This is accomplished by relative timing between aperture measurements. The car is then directed to its home position.

Referring to FIG. 5, apertures 54 on the top and bottom of track 15 define the specific home positions for cars 16 carrying pipettes 17A, B, and C. The home position for car 16 carrying pipette 17A is indicated at the right of FIG. 5 by the centerline which passes through the center of aperture 54 at the top of rail 15. This centerline passes through the left portion of aperture 54 at the bottom of rail 15. Since the bottom aperture is offset the sensors 55 on car 16 will see the apertures sequentially but the apertures are wide enough that in the exact home position both apertures will be seen. The home position for car 16 carrying pipette 17B is defined by the centerline passing through the exact center of both top and bottom apertures 54. The home position for car 16 carrying pipette 17C is defined by the centerline passing through the center of the top aperture and through the right portion of the bottom aperture.

In the preferred embodiment, the width of apertures 54 was chosen to be about 32 steps of stepper motor 42. This width is large enough to eliminate the possibility of a scratch on track 15 appearing as one of apertures 54. Also, it is wide enough to minimize the possibility of a foreign particle (dirt) blocking out an aperture 54. Exact stopping position within an aperture is determined by reflectively sensing the edge of the aperture, counting out 16 steps, and then halting. This procedure provides an excellent stop position resolution.

Referring to FIG. 6 the vertical position of automated pipette 17 is established by lead screw 57 and the step ratio of stepper motor 56. To avoid requiring position sensors, pipette mount plate 63 is driven downward against a hard stop 62 and stepper motor 56 is stepped additionally. When the direction is reversed, the beginning position is thus established by hard stop 62. The vertical position can never get lost since overstepping will result in pipette mount plate 63 contacting hard stop 62.

Advantages of the automated sample handling system include the ability to dilute a sample with either of two reagents and deliver a specific volume of that diluted sample to reaction cell 21. The system may also deliver a number of other reagents to reaction cell 21 depending upon the assay to be performed. Protein assays require only one more component, the antibody, while drug assays require drug conjugated to protein and antibody to be delivered. Hence, the sequence is modified from the protein sequence when drugs are assayed. The system also thoroughly rinses the reaction cell 21 after each assay. Pipette tips on automated pipettes 17 are also rinsed. The sample substances contact only the tip portions which are disposable and these tips may be replaced quickly if they become clogged or contaminated.

Removable tray sections 31 are disposable and one or more are easily inserted into and removed from turntable 19. Contamination of sample dilutions is therefore reduced. Automatic buffer delivery to reaction cell 21 after rinsing may be accomplished by plumbing buffer dispenser 25 into reaction cell 21 through pumps 22 and valves 23. The use of a data processor 26 to control the system sequence and interface with the operator allows minimal operator interface to set up the test sequence and unattended operation once the test sequence is established. Car 16 and track 15 are designed to be small, compact, and low cost. Motion control is accomplished with circuitry and programmed software through data processor 26. Complex functions are therefore performed by relatively simple mechanical design. The shapes, sizes, and extensions of this design can be modified for any desired application. The increased efficiency achieved by the invention reduces lead times and allows more accurate results in a shorter time.

In addition to economy of space and enablement of the single line car and track system, the use of one or more removable tray portions 31 in conjunction with turntable 19 has other functional advantages. The open center of turntable 19 could provide an area which could either rotate or remain stationary to house additional reagents and/or a wet sponge to help control humidity in the sample area. The turntable can interface with several automated reagent handling devices to dilute samples, pipette samples or to add reagent to the solutions which can then be incubated on the turntable and introduced into the measuring instrument at a later time. Removable tray portion 31 allows the immediate insertion of samples or the redefinition of sample dilution by inserting a new tray section 31. The interface between wells 34 and the inner row of concentric holes 28 in turntable 19 facilitates removal and insertion of tray sections 31. Positive alignment of removable tray sections 31 is assured because wells 34 in the last row of tray 31, extend downwardly from tray section 31, and are spaced apart a distance equal to the spacing between inner holes 28 for insertion therein. A number of tray sections 31 can thus be inserted into turntable 19 and turntable 19 is rotatable to allow pipettes 17A or B to access wells 34. Turntable 19 is positioned by conventional positioning means in response to signals from data processor 26.

Antigen excess dilution wells 20 are fixed and do not rotate with turntable 19. Dilutions of calibrator substance may be made into these cups to provide antigen excess checking solutions for those assays requiring antigen excess determination. Prediluting into these wells minimizes excess manipulation and increases efficiency by eliminating timing conflicts in cars 16 carrying sample to reaction cell 21.

While particular forms of the invention have been disclosed with respect to a preferred embodiment thereof, it is not to be so limited as changes and modifications may be made without departing from the scope of the invention. For example, while the invention has been disclosed as employed with a nephelometer, it may be advantageously employed with other testing apparatus. Any testing apparatus requiring handling and manipulations of a sample substance could advantageously employ this invention. In addition, turntable 19 could be replaced by a series of trays which move in alternate patterns. Track 15 could include a cable instead of the rail shown and cars 16 would be suspended therefrom. Track 15 need not be limited to a straight line configuration but could in fact be curved or angled.

The foregoing description, taken together with the appended claims, constitutes a disclosure which enables one skilled in the art and having the benefit of the teachings contained therein to make and use the invention. Further, the structure herein described constitutes a meritorious advance in the art which is unobvious to such skilled workers not having the benefit of these teachings.

What is claimed is:

1. A tray for use with an automated sample handling apparatus turntable, said turntable including a circular retaining rim, said circular retaining rim including at least one row of holes arranged in a circular configuration on said rim, said tray comprising a tray section configured as a segment of a circle, said tray section having a relatively narrow innermost width area and a relatively wide outermost width area, said tray section including a first row of wells configured in a relatively narrow arc in said narrow innermost width area and a last row of wells configured in a relatively wide arc in said wide outermost area, said wells formed as an integral part of said tray section and including well portions extending downwardly from said tray section, said last row of wells including a plurality of well portions spaced from each other and from an adjacent row of wells such that each said well portion in said last row is insertible into an adjacent hole in said row of holes in said rim, said tray section thereby retained by said rim.

* * * * *